United States Patent
Fitzpatrick

(10) Patent No.: US 10,058,357 B2
(45) Date of Patent: Aug. 28, 2018

(54) CONNECTOR FOR SPINAL IMPLANT SYSTEM

(71) Applicant: Fitzbionics Limited, Godalming, Surrey (GB)

(72) Inventor: Noel Fitzpatrick, Godalming Surrey (GB)

(73) Assignee: Fitzbionics Limited, Godalming, Surrey (GB)

( * ) Notice: Subject to any disclaimer, the term of this patent is extended or adjusted under 35 U.S.C. 154(b) by 0 days.

(21) Appl. No.: 15/121,802

(22) PCT Filed: Feb. 27, 2015

(86) PCT No.: PCT/GB2015/050570
§ 371 (c)(1),
(2) Date: Aug. 26, 2016

(87) PCT Pub. No.: WO2015/128664
PCT Pub. Date: Sep. 3, 2015

(65) Prior Publication Data
US 2017/0014162 A1   Jan. 19, 2017

(30) Foreign Application Priority Data
Feb. 28, 2014 (GB) .................................. 1403756.8

(51) Int. Cl.
A61B 17/70 (2006.01)
A61F 2/44 (2006.01)
A61B 17/80 (2006.01)

(52) U.S. Cl.
CPC ........ *A61B 17/705* (2013.01); *A61B 17/7001* (2013.01); *A61B 17/7005* (2013.01);
(Continued)

(58) Field of Classification Search
CPC .............. A61B 17/705; A61B 17/7001; A61B 17/7005; A61B 17/7019; A61B 17/7041; A61B 17/8042; A61F 2/446
(Continued)

(56) References Cited

U.S. PATENT DOCUMENTS

| 4,771,767 A | 9/1988 | Steffee |
| 5,810,817 A * | 9/1998 | Roussouly ......... A61B 17/7041 606/250 |

(Continued)

FOREIGN PATENT DOCUMENTS

| EP | 1500372 | 3/2005 |
| WO | 0200124 | 1/2002 |

(Continued)

OTHER PUBLICATIONS

Great Britain Search Report dated Jan. 12, 2015 in parent GB Application No. 1403756.8.
(Continued)

*Primary Examiner* — Pedro Philogene
(74) *Attorney, Agent, or Firm* — Andrus Intellectual Property Law

(57) ABSTRACT

A connector for a spinal implant system, the connector comprising a body portion and an extension portion, the body portion being adapted to couple thereto at least a first bone screw for installation in a vertebra, the body portion further being adapted for coupling at least a first elongate member thereto, the extension portion extending from the body portion, the extension portion being adapted for coupling thereto at least a first intervertebral device for installation in a spinal disc space. Preferably at least part of the extension portion is bendable.

21 Claims, 5 Drawing Sheets

(52) U.S. Cl.
CPC ...... *A61B 17/7019* (2013.01); *A61B 17/7041* (2013.01); *A61B 17/8042* (2013.01); *A61F 2/446* (2013.01)

(58) Field of Classification Search
USPC .......... 606/246–279, 68 A; 623/17.11–17.16
See application file for complete search history.

(56) References Cited

U.S. PATENT DOCUMENTS

| | | | | |
|---|---|---|---|---|
| 6,120,503 | A * | 9/2000 | Michelson | A61B 17/025 606/246 |
| 6,395,030 | B1 * | 5/2002 | Songer | A61B 17/70 623/17.11 |
| 2002/0107572 | A1 * | 8/2002 | Foley | A61F 2/446 623/17.11 |
| 2007/0213820 | A1 | 9/2007 | Magerl et al. | |
| 2008/0058805 | A1 * | 3/2008 | Stuart | A61B 17/7005 606/914 |
| 2009/0192613 | A1 * | 7/2009 | Wing | A61F 2/4465 623/17.11 |
| 2010/0228292 | A1 * | 9/2010 | Arnold | A61B 17/7005 606/264 |
| 2013/0035724 | A1 * | 2/2013 | Fitzpatrick | A61B 17/686 606/272 |

FOREIGN PATENT DOCUMENTS

| | | |
|---|---|---|
| WO | 2006084057 | 8/2006 |
| WO | 2008011492 | 1/2008 |

OTHER PUBLICATIONS

International Search Report dated May 15, 2015 in parent PCT Application PCT/GB2015/050570.

* cited by examiner

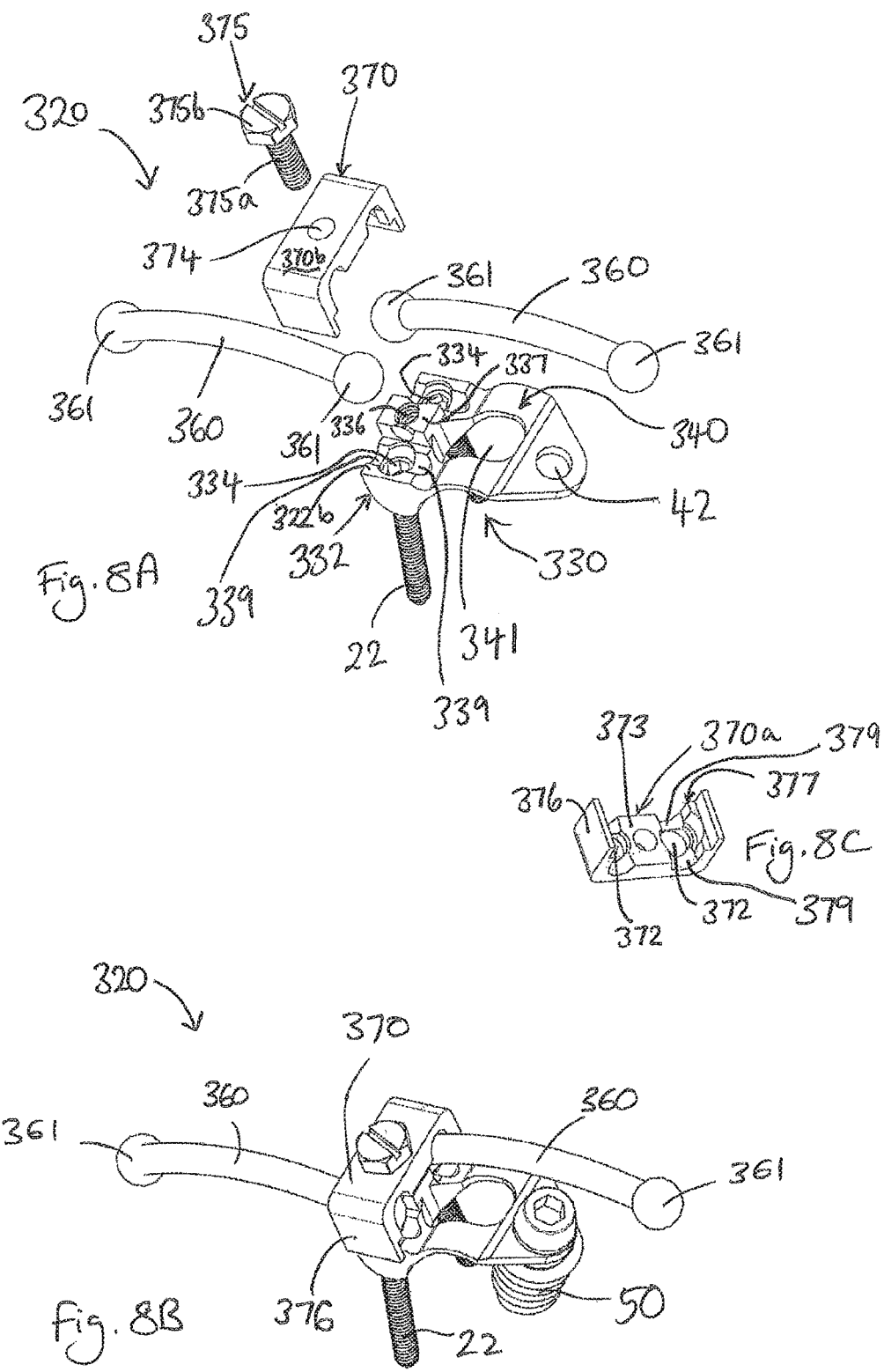

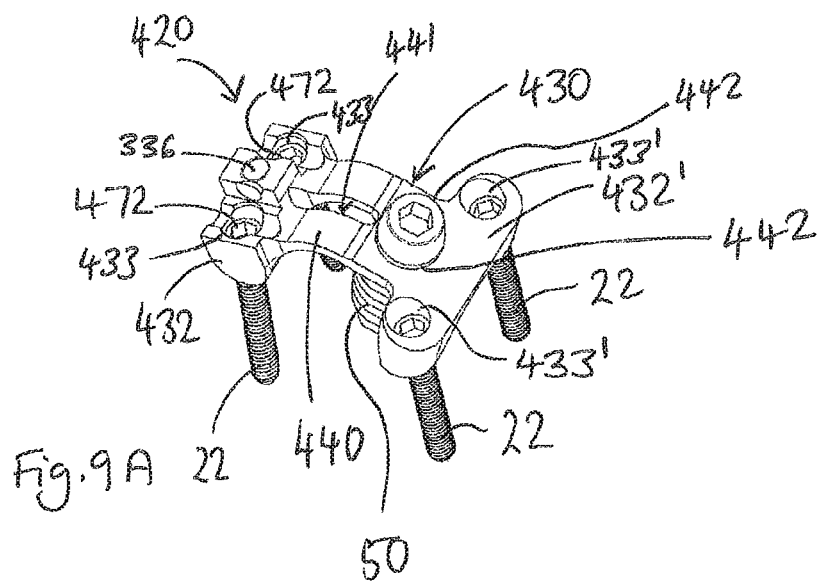
Fig. 9A
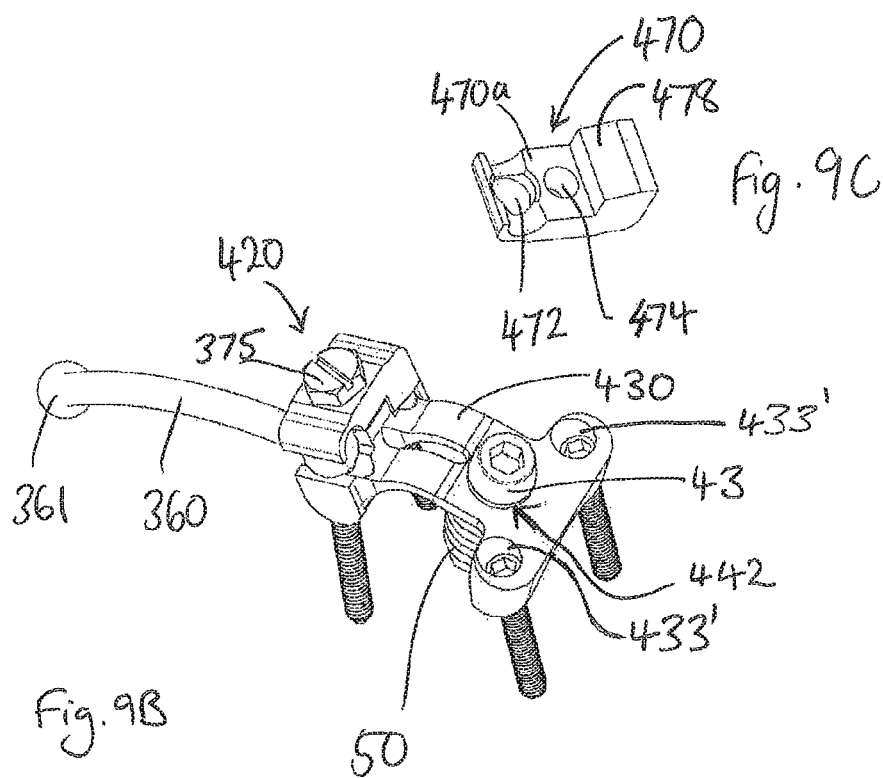
Fig. 9C
Fig. 9B

CONNECTOR FOR SPINAL IMPLANT SYSTEM

CROSS REFERENCE TO RELATED APPLICATIONS

The present application is the U.S. national stage application of International Application PCT/GB2015/050570, filed Feb. 27, 2015, which international application was published on Sep. 3, 2015 as International Publication WO 2015/128664 A1. The International Application claims priority of Great Britain Patent Application 1403756.8, filed Feb. 28, 2014, which was granted Jul. 20, 2016 as U.S. Pat. No. 2,524,883.

FIELD OF THE INVENTION

The invention relates to a connector for a spinal implant system and to spinal implant assemblies and systems incorporating the connector. More specifically the invention relates to a connector for coupling an intervertebral body to bone anchoring screws for fusing one or more vertebral joints and to assemblies and systems incorporating the connector.

BACKGROUND TO THE INVENTION

The spine or vertebral column comprises a plurality of separate vertebrae. The vertebrae are movable relative to one another, and separated from one another by fibrocartilage called intervertebral discs.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. The intervertebral discs provide mechanical cushion between adjacent vertebrae. Genetic or developmental irregularities, trauma, chronic stress, tumours, and disease, however, can result in spinal pathologies which either limit this range of motion, or which threaten the critical elements of the nervous system housed within the spinal column. A variety of systems have been disclosed in the art which achieve immobilization by implanting artificial assemblies in or on the spinal column.

In order to treat certain injuries or conditions of the spinal column an intervertebral device may be placed in the intervertebral disc space to fuse or promote fusion of adjacent vertebrae. Such fusion devices are often used in combination with stabilisation systems wherein a metal rod that is bendable to match the natural curvature of the spine is mechanically attached at strategically selected vertebrae, allowing the rod to be rigidly fixed to the spine. This provides a rigid support to the spinal column. For this, screws located in the bone structure are typically fixed to a specially designed clamp to attach to a spinal rod. A problem with these stabilisation systems if used in the cervical spine of small animals is that the space in this area is very limited and the quality of the underlying bone section is such that it is very difficult to achieve good fixation using cortical bone screws. There is the additional risk of screws being close to or damaging the nerves that are very close to the bone. A safer implant placement can be achieved from the ventral side where there is more bone structure for cortical screw placement. A fusion system that can be used in small animals, in particular for a ventral approach is needed, wherein confined spaces make conventional rod anchoring systems unsuitable.

SUMMARY OF INVENTION

According to a first aspect of the invention there is provided a connector for a spinal implant system, the connector comprising a body portion and an extension portion, the body portion being adapted to couple thereto at least a first bone screw for installation in a vertebra, the body portion further being adapted for coupling at least a first elongate member thereto, the extension portion extending from the body portion, the extension portion being adapted for coupling thereto at least a first intervertebral device for installation in a spinal disc space.

The connector is for an interbody vertebral implant assembly. The connector can be used with other connectors of the same or different types within a spinal implant system to fuse two adjoining vertebrae together, with an intervertebral device for installation in a spinal disc space between. The body portion has means for coupling at least one bone screw thereto to form an anchor device adapted for anchoring the connector to a first adjacent vertebra. The body portion has means for coupling a first elongate member thereto, the elongate member being for coupling a first connector to at least a second connector. The extension portion has means for selectively coupling an intervertebral device thereto, the intervertebral device being for insertion in an intervertebral space separating two adjacent vertebrae. The connector of the present invention, when used as part of a spinal fusion system, advantageously allows gradual build-up of the fusion system, piece by piece, making it easy to align and assemble the pieces in the confined space of the neck of a subject.

The extension portion has a longitudinal axis which is preferably configured to extend substantially parallel with the longitudinal axis of the subject's spine when installed. Advantageously, the connector is adapted so that it can be coupled to an intervertebral device after the intervertebral device has been installed in a subject (rather than requiring assembly to the intervertebral device before it is installed in the subject). This is because the connector is adapted to simply affix to the proximal end of the intervertebral device. Suitably the connector has means for holding the or each bone screw captive during installation of the bone screws in a subject.

The body portion is preferably configured to seat on the exterior surface of a vertebra when installed.

As used herein the term spinal disc space or intervertebral disc space refers to the space between adjacent vertebrae, which may or may not be occupied by an intervertebral disc.

The intervertebral device and at least one bone screw each have a longitudinal axis which is parallel to their direction of insertion in the spine. The connector is preferably configured to hold the longitudinal axis of the intervertebral device and at least one bone screw coupled thereto at a predetermined angle with respect to one another. The connector is preferably adapted to hold the longitudinal axis of the intervertebral device and at least one bone screw coupled thereto at a predetermined angle with respect to one another at least during and after installation in a subject. The predetermined angle can be selected or set depending on the particular vertebral geometry at the vertebral joint. This allows the intervertebral device to be anchored to an adjacent vertebra using the at least one bone screw, with the at least one bone screw stably anchored in the bone and with the body portion seated on said vertebra when installed, to provide a stable coupling. The predetermined angle may be varied by adjustment by the user or by selecting a connector from a set including connectors adapted to hold the longitudinal axes of the intervertebral device and at least one bone screw at differing angles relative to one another. Said predetermined angle is preferably adjustable.

Preferably at least part of the extension portion is bendable. This allows for adjustment of the angle that the longitudinal axes of the intervertebral device and the at least one bone screw will extend at with respect to one another when assembled to the connector. By means of the extension portion being bendable, this assists during installation in that a connector can be secured to an intervertebral device that has been installed in an intervertebral disc space and then the extension portion can be bent by the surgeon to place the bone screw or bone screws assembled to the connector stably into the adjacent vertebra whilst ensuring that the body portion is stably in contact with the vertebral bone underneath once the bone screws are installed. The extension portion is preferably bendable about an axis which is substantially parallel to the medio-lateral axis when the connector is installed. At least a portion of the extension portion is pivotable with respect to the body portion about an axis substantially parallel with the medio-lateral axis. The extension portion is preferably bendable such that with the distal end of the extension portion secured to the spine, the body portion of the connector can be bent towards or away from the spine. Alternatively, or in addition, a plurality of connectors can be provided to the installer as part of a modular kit in which connectors having extension portions at least a portion of which is bent at different angles relative to the body portion are provided and the user can select the connector which suits the vertebral geometry at the particular vertebral joint that the connector is being installed at. If using a modular kit of connectors providing differing angles for projection of the intervertebral device and at least one bone screw when assembled to the connector, at least a portion of the extension portion may be bendable to allow for fine adjustment of the angle between the intervertebral device and at least one bone screw prior to installation.

The extension portion is sized with a length to span between an implanted intervertebral device and a body portion implanted in an adjacent vertebra. Suitably the lateral width of the body portion is greater than that of the extension portion. This means that one or two elongate members can be assembled to the body portion to be positioned to one or both sides of the extension portion, substantially parallel with the extension portion, to couple the connector to another connector, to strengthen the bridge across the intervertebral space.

Preferably the extension portion is adapted to couple with the intervertebral device at or near the distal end of the extension portion. As used herein, the term distal or distally refers to location away from the point of attachment/connection of the corresponding piece with the remainder of the connector or assembly. As used herein, the term proximal or proximally refers to a location towards the point of attachment/connection of the corresponding piece with the remainder of the connector or assembly. At one end of the extension portion (the proximal end) is the body portion and at or near the other end (the distal end) of the extension portion is means for securing the extension portion to an intervertebral device.

Preferably the extension portion is an elongate plate. The connector is preferably configured such that the extension portion aligns substantially parallel with the coronal plane when installed. In an unbent configuration, the extension portion is planar. The planar extension portion can be bent out of the planar configuration by the installer or during manufacture.

Preferably the extension portion has an aperture for receiving a locking member for securing an intervertebral device to the extension portion. The aperture is preferably at or near the distal end of the extension portion. In preferred embodiments, the extension portion has a single aperture such that the extension portion is configured to couple to a single intervertebral device.

Preferably the extension portion is integral with the body portion. Alternatively the extension portion is attachable to the body portion. If so, the extension portion can be supplied pre-assembled to the body portion.

Preferably the body portion is adapted to couple thereto a second bone screw for installation in a vertebra. The body portion is adapted such that the second bone screw will be installed laterally from the first bone screw, both screws being installed in the vertebra. Preferably the body portion has a first aperture for receiving a first bone screw. Preferably the body portion has a second aperture for receiving a second bone screw.

Preferably the body portion has a lower surface adapted to face a vertebra when installed and an upper surface opposite said lower surface, the or each aperture for receiving a corresponding bone screw extending through the body portion from said upper surface to said lower surface, forming a bore for receiving at least a portion of the bone screw.

Preferably the body portion is adapted to couple thereto the or each bone screw at a predetermined angle relative to the body portion. The or each corresponding bore that receives the bone screw may be appropriately inclined relative to the body portion such that the bone screw will be correspondingly inclined when assembled to the body portion.

Preferably the body portion is adapted to couple thereto first and second bone screws, each at a predetermined angle relative to the body portion, the predetermined angles being such that the bone screws diverge from one another when installed. The bone screws preferably diverge from one another substantially in the transverse plane. Alternatively the bone screws can be installed such that they are convergent to one another. The body portion is preferably also adapted such that the first and second bone screws couple thereto with a predetermined spacing between the bone screws. Typically for a given type of animal, the desired angle of incline and lateral spacing for the first and second bone screws will not differ from one animal to another as the lateral geometry of vertebra in the cervical spine is typically quite consistent from one animal to the next.

Preferably the body portion has a first recess for receiving a first elongate member. Preferably the body portion has a second recess for receiving a second elongate member. The or each recess may be a groove. Alternatively, the or each recess may be a partially spherical shaped depression.

Preferably the body portion has a lower surface adapted to face a vertebra when installed and an upper surface opposite said lower surface, at least part of the lower surface of the body portion having a concave curvature. The concavely curved lower surface of the body portion is configured to conform to at least a portion of a subject's vertebra. The typical curvature of vertebra for a particular type of subject can be ascertained such that connectors with suitably curved body portions can be manufactured. Alternatively, custom-made body portions can be manufactured to suit a particular subject's vertebrae.

According to a further aspect of the invention there is provided a spinal implant assembly, the assembly comprising a connector according to any aspect of the invention as described above.

Preferably the assembly further comprises at least one bone screw for securing the connector to a first vertebra. The or each bone screw couples to the body portion when assembled as explained above. Bone screws for installation in vertebrae are well-known. Any suitable bone anchoring screws may be employed. Suitably at least part of the or each bone screw is externally threaded. Suitably the or each bone screw has a thin profile.

Preferably the assembly further comprises means for coupling the connector to a connector of another spinal implant assembly.

Preferably the assembly further comprises at least one elongate member for coupling to the body portion of the connector. The elongate member can couple the assembly to another assembly. Preferably the elongate member comprises a rod. Preferably the rod is bendable. Preferably the rod has first and second ends, one or both ends having an enlarged head. Preferably the or each enlarged head is a substantially spherical head. The body portion preferably includes at least one spherical shaped recess, the or each recess for receiving a spherical head of said rod therein. Preferably the radius of curvature of the recess is smaller than the radius of curvature of the corresponding spherical head of the rod to be received therein such that the body portion makes a circular line of contact with the spherical head when assembled.

Preferably the assembly further comprises an intervertebral device for securing the connector to a spinal disc space. When assembled, the intervertebral device is adapted to secure the connector to a spinal disc space adjacent the first vertebra that the bone screw is to be installed in.

Preferably at least part of the intervertebral device is externally threaded. Typically the or each bone screw will be narrower in profile than the intervertebral device, the or each bone screw being sized and shaped to install into bone and the intervertebral device being sized and shaped to install into intervertebral disc space. The intervertebral device will preferably have a hollow bore communicating with at least one aperture in its side. This allows for bone ingrowth into the intervertebral device when installed, thus improving the stability of the anchorage. Preferably at least part of the intervertebral device is hydroxyapatite coated.

Preferably the assembly further comprises a locking member for securing the intervertebral device to the extension portion. Preferably the locking member is adapted to secure the intervertebral device to the extension portion via a threaded connection. Preferably at least part of the locking member is externally threaded. Preferably the intervertebral device has a hollow bore. Preferably the locking member has a head portion and a shank portion, the shank portion being at least partially externally threaded, the intervertebral device having a bore with a first open end, the bore being at least partially internally threaded, the internal threads of the bore corresponding with the external threads of the shank portion of the locking member such that the locking member is attachable to the intervertebral device, with the extension portion retainable therebetween. The locking member may be releasably attachable to the intervertebral device. The locking member suitably retains the intervertebral device to the connector by means of the extension portion being clamped between the intervertebral device and the locking member when the pieces are assembled.

Preferably the assembly further comprises a clamp member for non-movably securing the or each elongate member to the connector. The clamp member acts as a compression member for securing the elongate member to the connector. Preferably the assembly further comprises a clamp locking member for non-movably securing the clamp member to the body portion. Suitably the clamp member is releasably attachable to the body portion. Preferably the clamp locking member is a locking screw, the locking screw having a shank, at least part of the shank being externally threaded, the body portion having a locking screw receiving bore with a first open end, the bore being internally threaded, the external threads of the bore corresponding with the external threads of the shank of the locking screw, the clamp member having a bore connecting first and second open ends, the locking screw being receivable in the bore of the clamp member and threadedly receivable in the bore of the body portion.

Preferably the clamp member has a lower surface adapted to face the connector when assembled and an upper surface opposite said lower surface, the lower surface including a first recess for receiving an elongate member therein when assembled. Preferably the lower surface has a second recess for receiving an elongate member therein when assembled. Suitably the recess(es) in the clamp member overlie corresponding recess(es) in the body portion when assembled, such that the or each pair of corresponding recesses can hold an elongate member captive therebetween. The or each recess in the clamp member may be a groove. The or each recess in the clamp member may alternatively by a spherical shaped depression. The or each spherical shaped depression in the clamp member is configured for receiving a spherical head of said elongate member therein. Preferably the radius of curvature of the or each spherical depression in the clamp member is smaller than the radius of curvature of the or each spherical head of the elongate member such that the clamp member makes a circular line of contact with the spherical head when assembled, to enhance fixation of the elongate member relative to the connector when the clamp member is non-movably secured to the connector.

Preferably the spinal implant assembly is a distal end assembly adapted to be installed in a subject distally to the distal end of an extension portion of a spinal implant assembly as described above, the distal end assembly adapted to be coupled to said spinal implant assembly, the distal end assembly being adapted to be installed with its extension portion extending towards the extension portion of the spinal implant assembly, the extension portion of the distal end assembly being adapted to couple with the extension portion of the spinal implant assembly. Suitably the extension portion of the distal end assembly is shorter than that of the standard connector. The extension portion of the distal end connector is sufficiently long to couple with the extension portion of a spinal implant assembly installed on an adjacent vertebra. An intervertebral device suitably couples to the extension portion of the spinal implant assembly and the distal end assembly when assembled.

According to a further aspect of the invention there is provided a spinal implant system comprising at least one spinal implant assembly as described above. Preferably the system comprises a first spinal implant assembly and a second spinal implant assembly comprising a distal end assembly, wherein first implant assembly is adapted to be secured to a first vertebra and the second spinal implant assembly is adapted to be secured to a second vertebra adjacent the first vertebra, and the intervertebral device of the first implant assembly is adapted to be secured in the spinal disc space between the first and second vertebrae, and wherein the first and second spinal implant assemblies are configured to be coupled together using an elongate member. The elongate member is suitably clamped at or near one end to the first implant assembly and clamped at or near the other end to the second implant assembly. The elongate member is positioned on the left or right lateral side of the intervertebral disc device when the assembly is installed. Where the second implant assembly is a distal end assembly, the extension portion of the distal end assembly couples with the extension portion of the adjacent spinal implant assembly when assembled.

Preferably the system comprises a plurality of spinal implant assemblies as described above, the spinal implant assemblies adapted to be assembled in a row with each spinal implant assembly secured to a vertebra of a row of successive vertebrae when installed and with the intervertebral device of each spinal implant assembly secured in the spinal disc space adjacent the corresponding vertebra such that the intervertebral devices are secured in a row of successive disc space when installed, the extension portions of the spinal implant assemblies extending substantially in the same direction as one another when the system is installed and wherein the spinal implant assemblies are adapted to be coupled together using an elongate member between each connector and the next connector. For example, each spinal implant assembly may be installed such that the proximal-distal axis of the extension portions substantially align with the cranial-caudal axis of the subject's spine. Of course, the row of assemblies need not be straight, and can be arranged to align with desired curvature of the fused vertebral region.

Preferably the system further comprises a distal end assembly for coupling to the spinal implant assembly at the distal end of the row of spinal implant assemblies relative to the direction of the extension portions thereof. This provides a stable end connection when assembling across one or more vertebrae pairs. Preferably the elongate members that couple the spinal implant assemblies together when assembled are arranged on alternate sides of the spine. In other words, a first elongate member may be on the left lateral side, then the next will be on the right lateral side, the next on the left lateral side and so on or vice versa. Instead of the elongate members being arranged alternately, elongate members can be assembled to couple a first spinal assembly to a second spinal assembly on both the right lateral and left lateral sides. In preferred embodiments, the elongate member for coupling a first spinal implant assembly to a second spinal implant assembly is sized such that the length of the elongate member is adapted to couple only two connectors together. In this way, spinal implant assemblies can be coupled together in a row, a pair at a time. Alternatively a longer elongate member which can couple more than two connectors together can be used to couple more than two connectors together, or to be cut down to size during installation to couple only two connectors together.

Advantageously the system may comprise two space-filling elongate members, one to be installed in each spinal implant assembly of a pair of assemblies or in each terminating spinal implant assembly of a row of assemblies. Each space-filling elongate member is sufficiently long to overlie the opening to the bone screw receiving bore in the body portion. Advantageously this fills the void where an elongate member for coupling to another connector could go and helps to prevent the underlying bone screw from loosening.

There is also provided a kit for assembly into a spinal implant assembly or system, wherein the kit comprises the parts of the assembly according to any previous aspect of the invention. Instructions for assembly may be provided as part of the kit.

A modular kit can be provided wherein differing connectors are provided. Connectors having body portions of differing lateral dimension can be provided, connectors having body portions with differing curvature of the lower surface can be provided. In particular, a range of connectors may be provided in a kit, the connectors having differing spacing between the bores for receiving first and second bone screws and/or differing angles of inclination of the bone screw bores such that the first and second bone screws diverge/converge from one another at differing angles. A plurality of each of the different connectors can be provided to allow for variations in bone geometry, entry approach etc.

There is also provided a computer program embodied on a computer readable medium for manufacturing a connector, spinal implant assembly or spinal implant according to any previous aspect of the invention.

There is also provided a method of installing a spinal implant system, the method comprising the steps of providing at least first and second implant assemblies according to any; implanting the intervertebral device of the first spinal implant assembly between adjacent vertebrae; coupling the intervertebral device to the extension portion of the connector of the first spinal implant assembly and securing the body portion to a vertebra adjacent the implanted intervertebral device; and coupling the connector to the second spinal implant assembly using an elongate member.

The term subject as used herein can be a human or animal subject. The terms lateral, ventral, dorsal, cranial, caudal as used herein have the usual meanings in relation to veterinary anatomy. For installation in a human subject, it will be understood that the terms ventral/dorsal as used herein can be substituted with the terms anterior/posterior. Anatomical directional terms used herein in relation to the connector, assembly or system refer to anatomical directions when the connector, assembly or system is installed in a subject. It will be understood that components of the invention can be positioned in a number of different orientations, the directional terminology being used for purposes of illustration and being in no way limiting.

BRIEF DESCRIPTION OF THE DRAWINGS

A preferred embodiment of the present invention will now be more particularly described by way of example only with reference to the accompanying drawings, wherein:

FIGS. 8A and 8B are perspective views of a spinal implant assembly according to a further embodiment, FIG. 8A being an exploded view of the assembly and FIG. 8B being an unexploded view of the assembly of FIG. 8A;

FIG. 8C is an underside perspective view of the clamp member of FIGS. 8A and 8B;

FIGS. 9A and 9B are perspective views of a spinal implant assembly according to a further embodiment which is suitable for implantation at the vertebral joint that forms the transition between the cervical and thoracic regions of the spine, FIG. 9A being an exploded view and FIG. 9B being an unexploded view of the assembly;

FIG. 9C is an underside perspective view of a clamp member of FIGS. 9A and 9B.

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 3A:
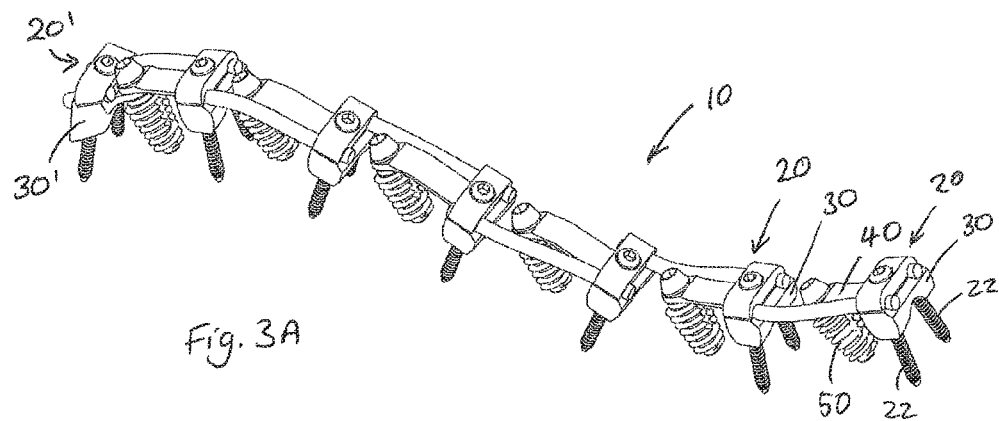
FIG. 3A is a perspective view of a spinal implant system comprising a plurality of spinal implant assemblies assembled in a row.

Referring to FIG. 3A, this shows a spinal implant system 10 according to the invention. This system can be used to fuse two or more vertebrae together, in order to provide stabilisation of the spine. The system of FIG. 3A comprises a plurality of individual spinal implant assemblies 20 which are assembled together in a series, end to end, with each assembly configured to secure to a vertebra and to an adjacent disc space of a successive row of vertebra. The system is particularly suited to achieving fusion of the cervical spine via a ventral approach, however it will be understood that it can be used at different regions of the spine and/or via a dorsal approach. The present invention is particularly suited for installation in small animals, where the confined space makes pre-existing systems unsuitable, however it will be understood that the present invention is also suitable for installation in humans.

Figure 1:
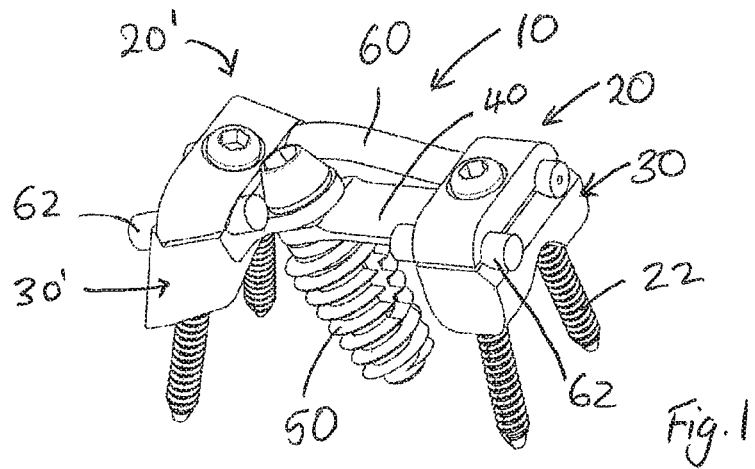
FIG. 1 is a perspective view of a spinal implant system 10 forming a bridge to fuse adjacent vertebrae.
Figure 2:
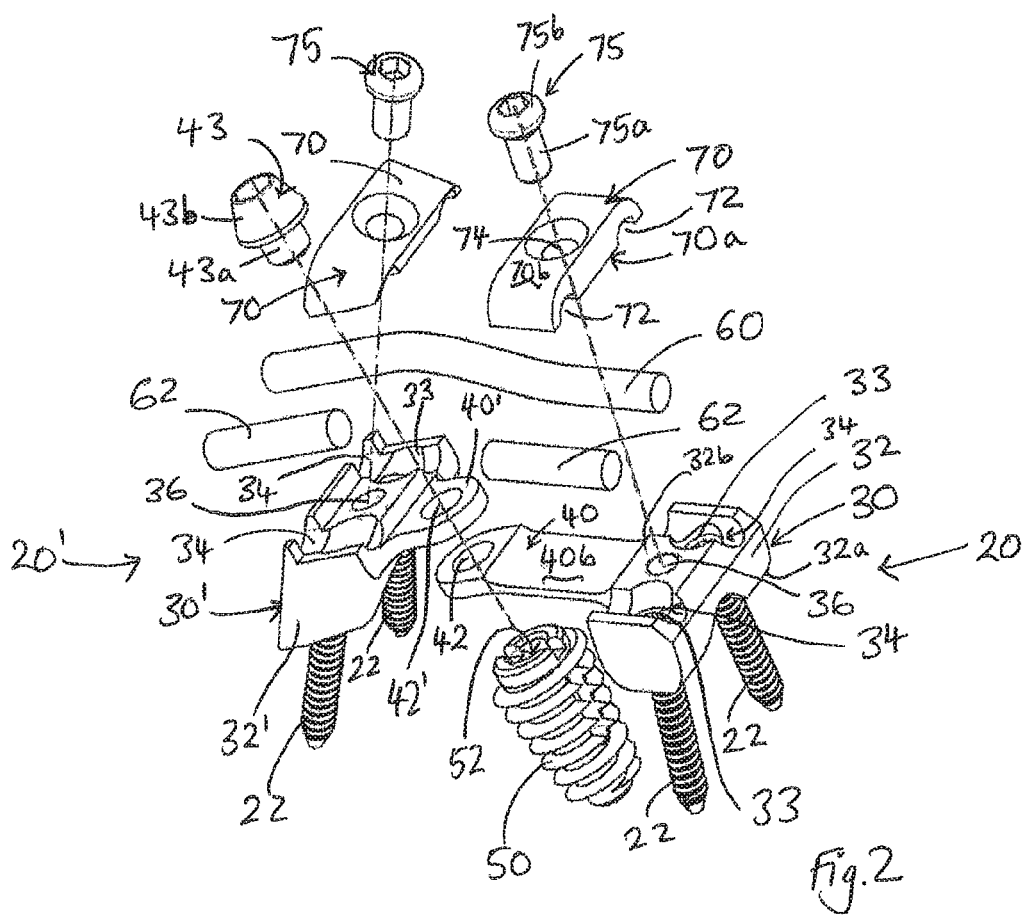
FIG. 2 is an exploded view of the system of FIG. 1.

FIGS. 1 and 2 show a shorter system of only two spinal implant assemblies 20, 20' for fusing two adjoining vertebrae. FIGS. 1 and 2 show a standard spinal implant assembly 20 on the right and a distal end assembly 20' shown on the left.

The standard spinal implant assembly 20 will now be described and will be referred to in the specification. The standard spinal implant assembly 20, shown on the right of FIGS. 1 and 2, comprises a connector 30, means for installation into vertebral bone comprising first and second bone screws 22, means for installation into the adjacent intervertebral disc space comprising an intervertebral device, and means 60 for coupling the connector 30 with another connector of another spinal implant assembly. In this embodiment the means for coupling the connector 30 with another connector is an elongate rod 60.

The connector 30 has a body portion 32 and an extension portion 40 extending from the body portion 32. The body portion 32 forms a saddle configured to contact the vertebra to which it is to be secured. The body portion has a lower surface 32a adapted to face a vertebra when installed and an upper surface 32b opposite said lower surface, at least part of the lower surface 32a of the body portion having a concave curvature configured to conform to at least a portion of a subject's vertebra.

The extension portion 40 is an elongate plate having an upper surface 40b adapted to face away from the spine when installed and a lower surface (not visible in the figures) opposite said upper surface. The extension portion 40 is preferably integral with the body portion 32 of the connector 30. The extension portion 40 is bendable such that during installation the connector 30 can be adjusted so that the body portion 32 can be stably seated on the vertebra relative to a coupled intervertebral device 50 that has already been installed in the disc space. The extension portion 40 is made from a suitable material that is sufficiently malleable to allow the extension portion 40 to be bent by the surgeon during installation, whilst retaining rigidity and strength once the connector 30 is fully installed.

The assembly 20 includes means for coupling the intervertebral device 50 to the extension portion 40, said means in this embodiment comprising a locking member 43 which is engageable with the intervertebral device 50 such that the extension portion 40 can be clamped therebetween. The locking member 43 has a head portion and 43b a shank portion 43a, at least part of which is externally threaded. The extension portion 40 has an aperture 42 at or near its distal end (i.e. the end furthest from the point at which the extension portion 40 meets the body portion 32 of the connector 30). The intervertebral device 50 has a hollow bore communicating with a first open end 52 in its proximal end (the end which secures to the extension portion 40), the bore being at least partially internally threaded such that the shank portion 43a of the locking member 43 can be threadedly secured to the intervertebral device 50. The locking member 43 is receivable through the aperture 42 in the extension portion and then securable in the first open end 52 of the intervertebral device 50 to secure the intervertebral device to the extension portion 40.

The body portion 32 has first and second bores 33 for receiving first and second bone screws 22 respectively. The bone screws 22 are preferably cortical screws. Each bore 33 extends from an aperture in the upper surface 32b to an aperture in the lower surface 32a of the body portion 32, forming a bore for receiving a corresponding bone screw 22. At least part of each bone screw 22 is externally threaded. The threading toward the distal end of each bone screw 22 will secure each bone screw 22 into vertebral bone when installed. Threading toward the proximal end of each bone screw corresponds with internal threading within each corresponding bore 33, such that the bone screws 22 lock securely relative to the connector 30 when installed. In alternative embodiments, the bone screws 22 may not be threadedly fastenable to the connector 30. Each bore 33 is inclined at a predetermined angle relative to the connector 30 such that when installed, the corresponding bone screw extends at a predetermined angle relative to the connector 30. In this particular embodiment the incline of the bores relative to the lateral axis of the connector 30 has been selected so that the first and second bone screws 22 of assembly 20 diverge from one another. Connectors can be provided with different spacings between the first and second bores 33 in the body portion 32 and with different inclines relative to the connector 30, so as to suit different vertebral bone geometry in different types of animal.

The connector 30 has means for non-movably securing the rod 60 for coupling the connector 30 with another connector of another spinal implant assembly. Said means comprises a clamp member 70 for clamping the rod 60 to the connector 30. The clamp member 70 has a lower surface 70a adapted to face the connector 30 when assembled and an upper surface 70b opposite the lower surface. The lower surface 70a has first and second grooves 72 shaped for receiving a rod thereunder. Similarly, the upper surface 32b of the body portion 32 of the connector 30 has corresponding first and second grooves 34 shaped for receiving a rod therein, each groove 34 extending across the upper open end of a bone screw receiving bore 33. The first and second grooves 72 of the clamp member 70 overlie the corresponding first and second grooves 34 of the connector 30 when assembled, allowing each pair of corresponding grooves to receive a rod 60 therebetween in the cylindrical space formed therein. The clamp member 70 is non-movably fastened to the connector 30 using a locking screw 75 (although other clamp locking means could be used). The locking screw 75 has a head portion 75b and a shank portion 75a, at least part of the shank portion 75a being externally threaded. The clamp member 70 has a bore 74 passing through it from an opening in the upper surface 70b to an opening in the lower surface 70a. During assembly, the shank portion 75a of the locking screw is received through bore 74 in the clamp member 70 and into an internally threaded bore 36 in the body portion 32, having a first opening in the upper surface 32b of the body portion 30, to threaddedly secure the clamp member 70 to the connector 30. If a rod 60 is placed in the first or second cylindrical space formed by grooves 34, 72, and the clamp member 70 then tightly fastened to the connector 30, the rod 60 will be clamped to the connector 30.

Figure 3B:
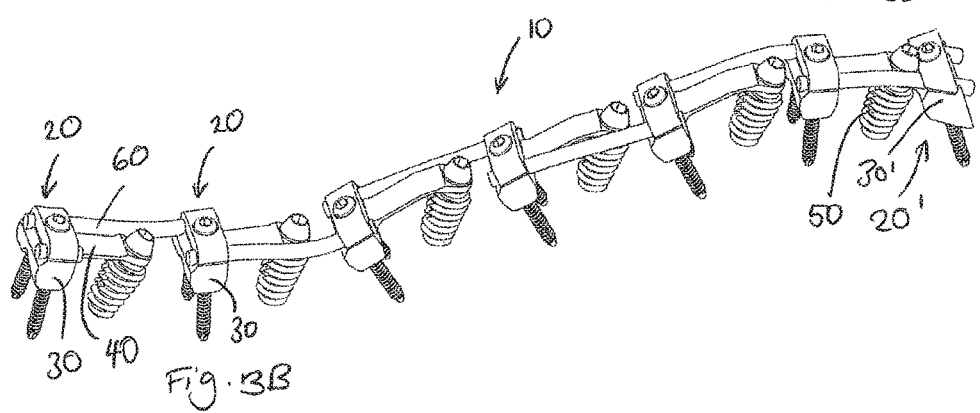
FIG. 3B is a further perspective view of the system of FIG. 3A, the system having been rotated around 180° in the plane of the page.
Figure 3C:
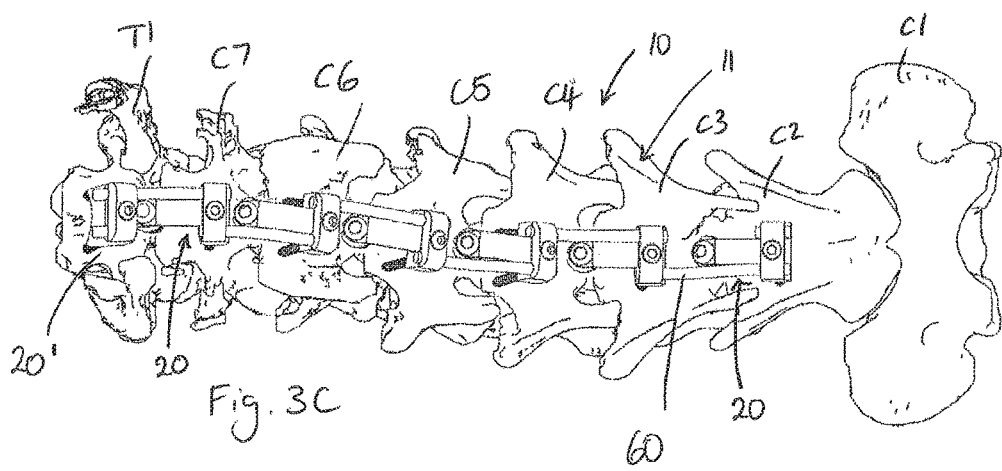
FIG. 3C is a ventral view of the system of FIG. 3A installed on a subject's cervical spine.

As can be seen from FIGS. 3A, 3B and 3C, several vertebral joints can be fused using a series of connectors 30, the connectors 30 being coupled to one another using rods 60 to strengthen the system. Starting at the right hand-side of FIG. 3A, there is a first connector 30 coupled distally to a second connector 30 (i.e. the second connector 30 is arranged distally of the distal end of the extension portion 40 of the first connector). The second connector 30 is coupled proximally to the first connector and distally to a third connector and so on.

In a spinal implant system of the present invention, any connector 30 which is not coupled distally to a further connector 30 of a standard spinal implant assembly is preferably coupled to a distal end assembly 20' in order to stabilise the intervertebral device 50 at the distal end of the system. For example, a distal end assembly 20' is assembled at the left-hand side of the row of implant assemblies in FIG. 3A and a distal end assembly 20' is preferably assembled to any standard spinal implant assembly used to fuse a single vertebral joint (for example, as shown in FIGS. 1 and 2).

A distal end assembly 20', as shown on the left of FIGS. 1 and 2, will now be described. The distal end assembly 20' is very similar to the standard spinal implant assembly 20 shown on the right of FIGS. 1 and 2, except that the distal end assembly 20' has a connector 30' with a shorter extension portion 40' than that of the standard assembly 20 and the distal end assembly 20' does not include its own intervertebral device for installation in the next disc space as the extension portion 40' of the distal end assembly 20' secures to the intervertebral device 50 associated with the adjacent standard spinal implant assembly 20 when assembled.

The distal end assembly 20' has a connector 30' having a body portion 32' and a short extension portion 40' extending therefrom. The body portion 32' is substantially similar to that of the standard spinal implant assembly 20 described above, said body portion 32' including first and second bores 33 for receiving first and second corresponding bone screws 22 for securing the connector 30' to a vertebra, first and second grooves 34 extending across each of the upper open ends of the bone screw bores 33 in the upper surface of the body portion 32', each able to receive a rod, and including a similar clamp member 70 and locking screw 75 adapted to clamp one or two rods against the connector 30'.

The extension portion 40' of the distal end connector 30' is a short plate-like piece having an upper surface adapted to face away from the spine when installed and a lower surface opposite the upper surface, adapted to face towards the spine when installed. The extension portion 40' has an aperture 42' passing through from the upper surface to the lower surface. The aperture 42' is sized to receive the shank portion 43a of the locking member 43 therethrough. The distal end connector 30' of the distal end assembly 20' is arranged distally of the standard spinal implant assembly 20 it is to couple to, with the extension portions 40, 40' of each connector 30, 30' pointing towards one another. In order to couple the connector 30 and distal end connector 30', extension portion 40' is placed over the distal end of extension portion 40, with the apertures 42', 42 aligned and the shank portion 43a of the locking member 43 is received through aperture 42', then through aperture 42 and secured in the threaded bore of the intervertebral device 50. Alternatively the distal end of extension portion 40 can be placed over extension portion 40' before connectors 30 and 30' are fastened together.

Similar to the connector 30 of a standard implant assembly 20, the extension portion 40' of the distal end connector 30' is bendable relative to the body portion 32' of the connector 30' so that the bone screws 22 received in body portion 32' can be placed into the vertebral bone with the lower surface of body portion 32' in stable contact with the bone.

An advantage of clamping the rod 60 which couples one connector to another to overlie the upper open end of bone screw receiving bore 33 is that this helps to prevent the bone screws 22 from unscrewing and therefore helps to prevent the bone screws from loosening from the bone. Referring to FIG. 3A, preferably each pair of implant assemblies 20, 20' is coupled together using a single rod 60, which is long enough to span the vertebral joint and to couple a connector installed in one vertebra to an adjacent connector installed in an adjacent vertebra. When a series of connectors are assembled end to end, the rods are preferably arranged on alternate sides of the system (for example, in the system of FIG. 3C, the first connector shown at the right hand side is coupled to the second connector by a rod arranged on the right lateral side of the spine and the second connector is coupled to the third connector by a rod arranged on the left lateral side and so on). In this arrangement one end of a rod 60 is received in the grooves 34, 74 in the body component 32, 32' and clamping member 70 on one side of the body portion 32, 32' and the other end of the rod is received in the grooves 34, 74 on the same side of the body component 32, 32' on the next connector.

Any connector 30, 30' which is only coupled to one other connector preferably has a short rod 62 assembled within the groove 34 which is not used for coupling to another connector. The system of FIG. 1 shows a pair of implant assemblies 20, 20' having a short rod 62 assembled within a groove 34 of each connector. The short rods 62 serve to prevent the bone screws 22 from unscrewing, in the same way that rod 60 of the system does.

Referring to FIG. 3C, the system of FIGS. 3A and 3B is shown installed on the ventral side of a subject's spine 11. The vertebrae are labelled and as can be seen, starting from the right hand side, the bone screws of the first spinal implant assembly are installed at vertebra C2, with its intervertebral device installed in the disc space between vertebrae C2 and C3, the bone screws of the second spinal implant assembly are installed in vertebra C3, with its intervertebral device installed in the disc space between vertebrae C3 and C4 etc. The seventh assembly is a distal end assembly 20', having its bone screws installed in vertebra T1 and its extension portion extending towards vertebra C7.

Referring to FIGS. 4 to 7, various different connectors are shown. In FIGS. 4A and 4B a connector 130 is shown wherein the distal end of its extension portion 140 is bent relative to the longitudinal axis of the extension portion. The extension portion 140 extends from the body portion 132 such that the longitudinal axis of the extension portion 140 is perpendicular to that of the bone screws 22 when installed (i.e. the longitudinal axis of the extension portion 140 extends from the body portion 132 with the longitudinal axis of the extension portion 140 perpendicular to that of the bores for the bone screws). The distal end of the extension portion 140 is bent in a direction towards the spine when installed, such that the distal end of the intervertebral device 50 points towards the bone screws 22. A notional angle between the intervertebral device 50 and the bone screws 22 in the sagittal plane is an acute angle (i.e. the distal ends of the intervertebral device 50 and the bone screws 22 are convergent).

Figure 4A:
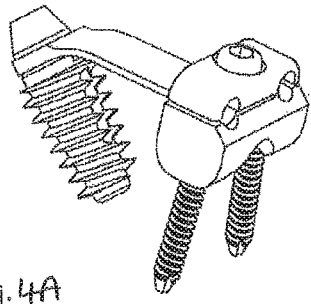
FIGS. 4A and 4B are perspective and side views respectively of a spinal implant assembly having a bent extension portion.
Figure 4B:
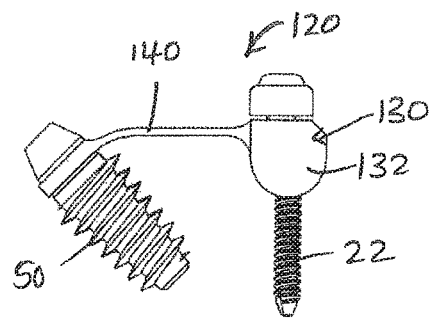
Figure 5A:
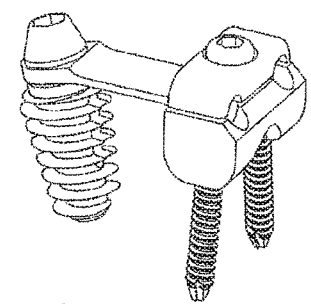
FIGS. 5A and 5B are perspective and side views respectively of a spinal implant assembly having a straight extension portion.
Figure 5B:
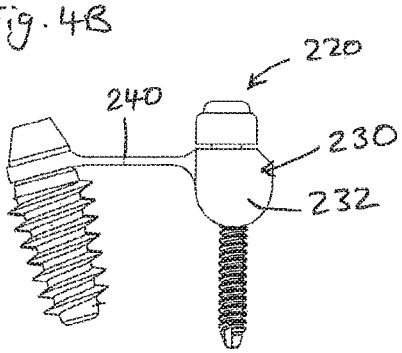

In FIGS. 5A and 5B a connector 230 is shown wherein the distal end of its extension portion 240 is bent relative to its connection with the body portion 132, towards the spine, however it is bent by a smaller angle than the connector 140 of FIGS. 4A and 4B. The extension portion 240 of the variant in FIGS. 5A and 5B is also shorter than the extension portion 140 of the FIG. 4A, 4B, connector 130. A connector 30 for a standard spinal implant assembly 20 preferably is bendable such that only the distal, apertured part, of the extension portion 40 bends relative to the body portion 32.

Figure 6A:
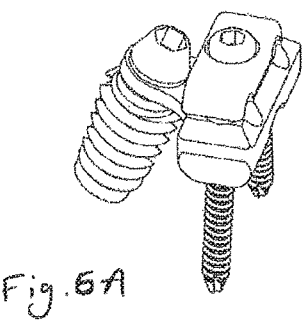
FIGS. 6A and 6B are perspective and side views respectively of a distal end assembly.
Figure 6B:
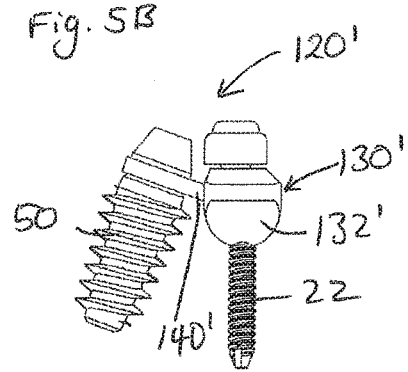

FIGS. 6A and 6B show a connector 130' for a distal end assembly 120', the extension portion 140' being angled away from the spine about its connection with the body portion 132', such that a notional angle between the intervertebral device 50 and the bone screws 22 in the sagittal plane is an obtuse angle (i.e. the distal ends of the intervertebral device 50 and the bone screws 22 are divergent).

Figure 7A:
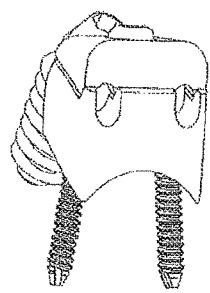
FIGS. 7A, 7B, and 7C are a rear perspective view, side view, and front perspective view respectively of another embodiment of a distal end assembly
Figure 7B:
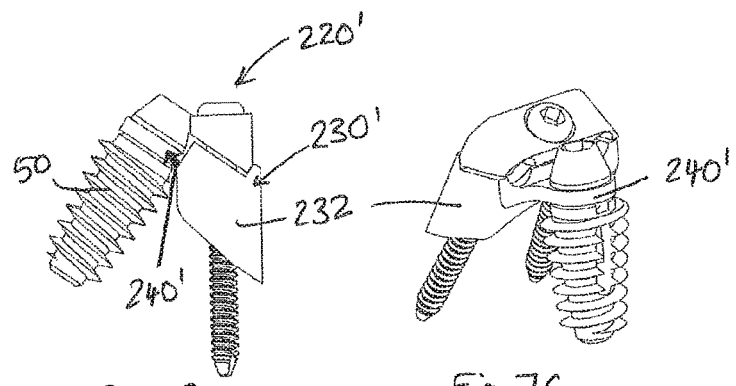
Figure 7C:
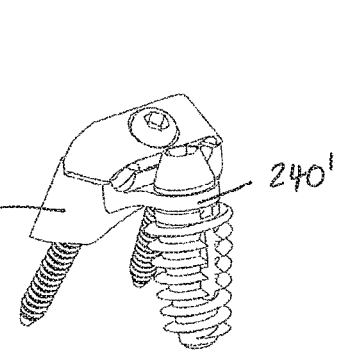

FIGS. 7A, 7B and 7C show another example connector 230' for a distal end assembly 220', the extension portion 240' being angled away from the spine about its connection with the body portion 132', but with the extension portion 240' angled at a greater angle relative to the bores for the bone screws 22 than in the connector 130' of FIGS. 6A and 6B, such that the intervertebral device 50 and the bone screws 22 are diverge by a larger angle in FIGS. 7A, 7B and 7C.

The rods 60 for coupling one connector to another are preferably bendable so that the installer can bend the rods during assembly.

In operation, in order to install a system according to the present invention an intervertebral device 50 is inserted in between two adjoining vertebrae by drilling through the intervertebral disc. A spinal implant assembly 20 is then placed on top of the intervertebral device 50 and the intervertebral device 50 is secured to the distal end of the extension portion 40 of the connector 30. The connector 30 is then secured to a vertebra adjacent the disc space. The extension portion 40 can be bent to place the bone screws 22 through the vertebral body into each pedicle whilst making sure the lower surface of the body portion 32 makes stable contact with the bone underneath. The spinal implant assembly can be coupled to an adjacent spinal implant assembly that has been installed distally using one or two rods 60 to strengthen the bridge formed across the vertebral joint. By installing several spinal implant assemblies in series in this manner, several vertebral joints can be used and linked using an alternate arrangement of rods.

In operation to install a distal end assembly 20' (i.e. in situations where only a single vertebral joint is to be fused by a standard spinal implant assembly 20 and a distal end assembly 20' or in situations where several vertebral joints are to be fused and a distal end assembly is required to stabilise the distal end of the row of connectors), a distal end assembly 20' is placed adjacent a standard spinal implant assembly 20, each overlying an adjacent vertebra, and the extension portions 40, 40' of each are secured to an intervertebral device installed in the disc space between. Then each connector 30, 30' is secured to its corresponding vertebra using bone screws and the connectors 30, 30' are coupled using a rod 60.

Preferably the intervertebral device 50 is a specially designed device, such as a disc screw, disc bolt or other spacer for installation between two adjoining vertebrae. In the presently described embodiment the intervertebral device 50 is externally threaded and these threads on the external surface cut into the tissue during insertion. The intervertebral device 50 has a hollow bore. The intervertebral device 50 has at least one elongate slot communicating with the hollow bore, the or each slot having a longitudinal axis running parallel with the longitudinal axis of the intervertebral device 50. The outer surface of the intervertebral device 50 may have a hydroxyapatite coating to stimulate bone ingrowth. The hollow bore of the intervertebral device 50 can be impregnated with bone graft before installation in the subject. The subject's bone will ingrow, through the elongate slot(s), and attach with the bone graft inside the hollow section. This further anchors the device in the subject. Even if no bone graft is inserted in the hollow of the device before implantation, cutting of the subject's bone by the external threads as the device is implanted will create bone debris that will accumulate, via the elongate slot(s), in the hollow bore. The subject's bone will ingrow, through the elongate slots(s) and attach with the accumulated bone debris, further anchoring the device against rotation.

As well as the lower surface of the body portion 32, 32' of a connector 30, 30' being concavely curved or at least partially concavely curved in the transverse plane, the lower surface may be convexly curved in the coronal plane for optimal seating over a range of bony geometries.

Instead of being bendable by the user during installation, the extension portion 40,40' of a connector 30, 30' can be provided as part of a kit in which connectors having extension portions bent at different angles relative to the body portion are provided and the user can select the connector which suits the vertebral geometry at the particular vertebra that the connector is being installed at.

Referring to FIGS. 8A-8C, a further embodiment of a spinal implant assembly is shown. FIGS. 8A and 8B show a standard spinal implant assembly 320 like standard spinal implant assembly 20 of FIG. 1 (i.e. a standard spinal implant assembly that can be coupled to a series of other standard spinal implant assemblies installed longitudinally along a subject's spine, as shown for example in FIG. 3C). The same reference numerals have been used in the Figures for features which are substantially the same as features of other embodiments. The standard spinal implant assembly 320 of FIGS. 8A and 8B is similar to that of FIG. 1 except for certain differences which will be described.

The spinal implant assembly 320 includes a connector 330 having a body portion 332 that receives first and second bone screws 22. The extension portion 340 is an elongate plate which extends from the body portion 332 and which differs from that of the FIG. 1 embodiment in that the extension portion 340 is wider than that of the FIG. 1 embodiment and extension portion 340 is provided manufactured in a pre-bent form wherein the plate is curved in the sagittal plane such that the plate is hump shaped. The extension portion 340 is a thin plate of substantially uniform thickness having a lower surface adapted to face the spine when installed and an upper surface opposite said lower surface, the upper surface being convexly curved in the sagittal plane and the lower surface being concavely curved in the sagittal plane.

The extension portion 340 has an aperture 42 at or near its distal end for coupling an intervertebral device 50 (shown in FIG. 8B) to the connector 330. The extension portion 340 has slot 341 therein, which in the present embodiment is an elongate slot having an elongate axis parallel with the sagittal plane, but which may be other shapes. The slot 341 decreases the stiffness of extension portion 340 compared to an extension portion without any slot, therefore making it easier for a user to bend the extension portion 340 to vary the curvature of extension portion 340 from that shown in FIG. 8A in order to selectively increase or decrease the angle between the longitudinal axes of the bone screws 22 and intervertebral device relative to one another when assembled such that the bone screws 22 and intervertebral device are angled relative to one another to suit the geometry at the vertebral joint where the assembly is to be installed. The curvature of extension portion 340 in the sagittal plane also provides space to accommodate vertebral bone beneath it when installed, thus allowing the assembly to be installed on the spine without the need to cut large amounts of vertebral bone to accommodate the connector 330.

In this embodiment the means for coupling the connector 330 with another connector is an elongate rod 360 like that of the previous embodiments except that the elongate rod 360 has a ball end 361 at each end of the rod, each ball end 361 being substantially spherical.

Like the connector of the FIG. 1 embodiment, the spinal implant assembly 320 has means for securing the rod 360 to the connector 330, said means being a clamp member 370 for clamping the rod 360 to the connector 330. The clamp member 370 has a lower surface 370a adapted to face the connector 330 when assembled and an upper surface 370b opposite the lower surface. The lower surface 370a has first and second recesses 372 each for receiving the spherical end 361 of a rod 360 thereunder. Similarly the upper surface 332b of the body portion 320 of the connector 330 has corresponding first and second recesses 334 for receiving the spherical end 361 of a rod 360 therein. The first and second recesses 372 of the clamp member 370 overlie the corresponding first and second recesses 334 of the connector 330 when the clamp member 370 is assembled thereto, allowing each pair of corresponding recesses to receive a spherical end 361 in the space formed therebetween. The clamp member 370 is non-movably fastenable to the connector 330 using a locking screw 375 (although other clamp locking means could be used). The locking screw 375 has a head portion 375b and a shank portion 375a, at least part of the shank portion 375a being externally threaded and receivable in a bore 374 passing through the clamp member 370 and an internally threaded bore 336 in the connector 330 to threadedly secure the clamp member 370 to the connector 330 with the end of a rod 361, or two rod ends, clamped therebetween.

Whereas the connector and clamp member of the FIG. 1 embodiment had cylindrical grooves for receiving rods, the recesses 334, 372 in the connector 330 and clamp member 370 in the FIG. 8 embodiment are preferably part-spherical depressions. The recesses 334, 372 in the connector and clamp member are each concavely curved and the curvature of each recess 334, 372 is substantially the same as one another. The curvature of each recess 334, 372 may closely match that of the spherical end 361 of the rod 360 to be received therein. Preferably however the curvature of the recesses 334, 372 does not match the spherical end 361 to be received therein and instead the radius of curvature of the recesses 334, 372 is slightly less than the radius of curvature of the spherical end 361 of the rod. This non-conformance between the radius of curvature of each substantially spherical end 361 of the rod and the concave recesses 334, 372 provides an edge contact between the spherical rod end 361 and the edge of the recess 334, 372. The edge contact between the edge of each recess and a corresponding spherical end 361 of the rod comprises a circular line of contact, which enhances the fixation of the rod 360 relative to the connector 330 and reduces loosening. For example, the radius of curvature of the recesses 334, 372 may be around 0.5 mm less than the radius of curvature of the spherical end 361 of rod 360.

Between the first and second recesses 334 of the upper side of the body portion of the connector 330 is a wall portion 337 in which bore 336 is located. There is a corresponding wall portion 373 on the lower surface 370a of the clamp member 370 in which bore 374 is located. Wall portions 337 and 373 preferably do not engage one another when the clamp member 370 is clamped relative to the connector 330 in order to clamp at least one spherical end 361, and preferably a small gap is maintained between wall portions 337 and 373. The clamp member 370 has first and second lateral side walls 376 which extend away from the main body of the clamp member 370 and towards the spine when installed. On the inner side of each lateral side wall 376 is a shoulder 377 which preferably does not engage the upper surface 332b of the body portion 332 of the connector 330 when the clamp member 370 is assembled to the connector 330 with at least one spherical end 361 clamped therebetween. When the clamp member 370 is assembled to the assembly as shown in FIG. 8B, the lateral side walls 376 of clamp member 370 overhang the side of the body portion of connector 330. By means of the lateral side walls 376 overhanging the connector 330, this helps the user to locate the clamp member 370 into the correct position with respect to the connector 330.

As can be seen in FIG. 8A, there is a first notch 339 (i.e. a cut-out) extending proximally and a second notch 339 extending distally away from each recess 334 in the connector. Similarly, there are corresponding notches 379 extending proximally and distally from each recess 372 in the clamp member 370. The notches 339, 379 allow for the rod 360 to be angled at a greater range of angles relative to the connector 330.

Each rod 360 has a length such that it will span between a first connector 330 to be installed in a first vertebra and a second connector 330 to be installed in an adjacent vertebra. A set of matching rods 360 may be supplied having a length predetermined based on the subject the assembly is to be installed in. Alternatively a kit may be supplied with rods 360 of differing discrete lengths. The rods 360 are preferably bendable to conform to the natural curvature of the spine. Slight bending of the rod 360 also provides a small reduction in length between the two spherical ends 361 of a rod 360 to precisely position the spherical ends 361 into the corresponding recesses 334 and 372 of the two adjacent standard assemblies 320.

Referring to FIGS. 9A and 9B, a further embodiment of a spinal implant assembly 420 is shown which is intended for implantation at the vertebral joint that forms the transition between the cervical and thoracic regions of the spine (i.e. for implantation across the joint between the C7 and T1 vertebrae). The assembly 420 is somewhat like the bridge formed by the standard spinal implant assembly 20 and the distal end assembly 20' as shown in FIG. 1, except that in the FIG. 9 embodiment the bridge is formed by a single connector 430 which is secured to both adjacent vertebrae spanning the vertebral joint to be fused, rather than by two connectors which are coupled together across the vertebral joint by one or more rods. The connector 430 comprises a first body portion 432 and a second body portion 432' which are coupled by an extension portion 440. In this embodiment the extension portion 440 is integral with the first and second body portions 432, 432', however the components may be initially separate and affixed together in a suitable manner. The first body portion 432 has means for installation into vertebral bone, which in this embodiment is via means of two bone screws 22 each receivable in a corresponding bore 433 in the first body portion 432. Similarly the second body portion 432' has two bores 433', each for receiving a bone screw 22 to be implanted in the adjacent vertebral bone.

Like the extension portion of the FIG. 8 assembly, the extension portion 440 of the FIG. 9 assembly is an elongate plate. Preferably the extension portion 440 is provided in a pre-bent form as shown in FIGS. 9A and 9B wherein the plate is curved in the sagittal plane such that the plate is hump shaped. The extension portion 440 has a smaller thickness than the body portions 432, 432' and the extension portion 440 also includes a slot 441 therein, both of which allow for the extension portion 440 to be malleable so that it can be bent to change the curvature of the extension portion 440 and to change the angle at which the proximal bone screws 22 extend relative to the distal bone screws 22. The extension portion 440 includes an aperture 442 therein for receiving the intervertebral device 50 so that the intervertebral device 50 can be securely engaged with the connector 430. The aperture 442 for receiving the intervertebral device 50 is nearer the distal end of the device than the proximal end, i.e. nearer the second body portion 432' than the first body portion 432. Like the FIG. 8 assembly, the curved extension portion 440 provides space for vertebral bone to reside underneath so that the assembly can be installed without removing excessive amounts of bone.

The spinal implant assembly 420 is adapted for securing at least a first rod 360 to the connector 430. The upper surface of the first body portion 432 is configured like that of the upper surface of the body portion of the FIG. 8 embodiment (i.e. including first and second recesses 472 for receiving the spherical end of a rod 360). In this embodiment, the second body portion 432 does not include any recesses on its upper surface and is therefore not configured to couple any rods thereto. The assembly 420 includes a clamp member 470 for clamping a rod 360 to the connector 430. The clamp member 470 differs from that of the FIG. 8 embodiment in that the clamp member 470 is configured for clamping only one rod 360 to the connector 430. At one lateral end, the clamp member 470 has a single recess 472 in its lower surface 470a adapted to face the connector 430 for receiving the spherical end of a rod 360 thereunder. At the other lateral end there is a protrusion 478 extending away from the lower surface 470a of the clamp member 470, intended to seat over the recess 472 in the connector 430 which does not receive a rod 360 in use. The clamp member 470 includes a bore 474 for receiving a locking screw 375 for securing the clamp member 470 to the connector 430 to clamp the rod 360 therebetween. The assembly 420 may be coupled to a spinal implant assembly such as the type shown in FIG. 8B using a rod 360, or alternatively the assembly 420 may be installed at the C7-T1 joint without coupling the assembly 420 to any other spinal implant assemblies. Of course, this connector 430 could of course alternatively be used to couple two rods thereto by using a clamp member 370 as shown in FIG. 8 instead of clamp member 470, whereby both rods run side by side to join assembly 420 to an adjoining standard assembly 320. This assembly with single connector 430 for installation at the C7-T1 joint provides a stable device for fusion of the joint.

It will be understood that changes may be made in the details of the invention without departing from the spirit of the invention, especially as defined in the following claims.

The invention claimed is:

1. A spinal implant system for fusing two adjacent vertebrae of a subject's spinal, the spine implant system comprising:
   a first intervertebral device for installation in a spinal disc space,
   a first elongate member,
   a first connector and a second connector, each comprising a body portion,
   being adapted to couple thereto at least a first bone screw for installation in a vertebra, the body portion further being adapted for coupling said first elongate member thereto,
   the first connector further comprising an extension portion extending from the body portion, the extension portion being adapted for coupling thereto at least a first intervertebral device for installation in a spinal disc space,
   wherein at least part of the extension portion is bendable, the extension portion having a longitudinal axis which is configured to extend substantially parallel with the longitudinal axis of the subject's spine when installed;
   said first intervertebral device being coupled in use to the extension portion of the first connector at or near the distal end of the extension portion,
   the first and second connectors being coupled together in use by said first elongate member, and
   the spinal implant system being capable of being installed without the intervertebral device being coupled to the second connector.

2. A spinal implant system according to claim 1, wherein the extension portion is an elongate plate.

3. A spinal implant system according to claim 1, wherein the extension portion has an aperture for receiving a locking member for securing the intervertebral device to the extension portion.

4. A spinal implant system according to claim 1, wherein the extension portion is integral with the body portion.

5. A spinal implant system according to claim 1, wherein the body portion of each connector is adapted to couple thereto first and second bone screws, each at a predetermined angle relative to the body portion, the predetermined angles being such that the bone screws diverge from one another when installed.

6. A spinal implant system according to claim 1, wherein the body portion of each connector has a first recess for receiving a first elongate member.

7. A spinal implant system according to claim 6, wherein the body portion of each connector has a second recess for receiving a second elongate member.

8. A spinal implant system according to claim 6, wherein the recess is a groove.

9. A spinal implant system according to claim 6, wherein the recess comprises a partially spherical shaped depression.

10. A spinal implant system according to claim 1, wherein the body portion of each connector has a lower surface adapted to face a vertebra when installed and an upper surface opposite said lower surface, at least part of the lower surface of the body portion having a concave curvature.

11. A spinal implant system to claim 1, wherein the lower surface of the body portion of each connector is configured to conform to at least a portion of a subject's vertebra.

12. A spinal implant system according to claim 1, wherein the elongate member comprises a rod.

13. A spinal implant system according to claim 12, wherein the elongate member has first and second ends, one or both ends having an enlarged head.

14. A spinal implant system according to claim 13, wherein the or each enlarged head is a substantially spherical head.

15. A spinal implant system according to claim 1, wherein at least part of the intervertebral device is externally threaded.

16. A spinal implant system according to claim 11, wherein each connector further comprises a clamp member for non-movably securing the first elongate member to the connector.

17. A spinal implant system according to claim 1, the implant system further comprising a plurality of additional connectors, each additional connector having the features of the first connector, the first, second and additional connectors being adapted to be assembled in a row with each connector secured to a vertebra of a row of successive vertebrae when installed, the system comprising an intervertebral device coupled in use to each connector, each intervertebral device being secured in the spinal disc space adjacent the corresponding vertebra such that the intervertebral devices are secured in a row of successive disc space when installed, the extension portions of the connectors extending substantially in the same direction as one another when the system is installed and wherein the connectors are adapted to be coupled together using an elongate member between each connector and the next connector.

18. A spinal implant system according to claim 1, wherein the intervertebral device is not coupled in use to the second connector.

19. A spinal implant system according to claim 1, wherein the second connector further comprising an extension portion extending from the body portion, where said extension portion on the second connector is shorter than the extension portion of the first connector, and the intervertebral device is coupled in use to the extension portion of the second connector in addition to being coupled to the extension portion of the first connector.

20. A spinal implant system according to claim 17, the system further comprising a plurality of elongate members, each elongate member coupling a pair of adjacent connectors in use, the successive elongate members in the row being arranged on alternate sides of the row of connectors.

21. A spinal implant system according to claim 16, wherein the clamp member of each connector is configured to non-movably secure the first elongate member and a second elongate member to the connector.

* * * * *

UNITED STATES PATENT AND TRADEMARK OFFICE
CERTIFICATE OF CORRECTION

PATENT NO. : 10,058,357 B2  
APPLICATION NO. : 15/121802  
DATED : August 28, 2018  
INVENTOR(S) : Noel Fitzpatrick Page 1 of 1

It is certified that error appears in the above-identified patent and that said Letters Patent is hereby corrected as shown below:

In Claim 1, Column 18, Line 23, "subject's spinal" should instead read --subject's spine--

In Claim 1, Column 18, Line 23, "spine implant system" should instead read --spinal implant system--

Signed and Sealed this  
Thirteenth Day of November, 2018

Andrei Iancu  
*Director of the United States Patent and Trademark Office*